(12) United States Patent
Inosaka et al.

(10) Patent No.: US 8,409,609 B2
(45) Date of Patent: Apr. 2, 2013

(54) PERCUTANEOUS ABSORPTION-TYPE PHARMACEUTICAL PREPARATION

(75) Inventors: Keigo Inosaka, Ibaraki (JP); Junichi Sekiya, Ibaraki (JP); Akio Takada, Ibaraki (JP); Toshinobu Tsuda, Ibaraki (JP)

(73) Assignee: Nitto Denko Corporation, Osaka (JP)

( * ) Notice: Subject to any disclaimer, the term of this patent is extended or adjusted under 35 U.S.C. 154(b) by 1008 days.

(21) Appl. No.: 11/446,125

(22) Filed: Jun. 5, 2006

(65) Prior Publication Data

US 2006/0275354 A1 Dec. 7, 2006

(30) Foreign Application Priority Data

Jun. 6, 2005 (JP) .............................. P. 2005-165213

(51) Int. Cl.
*A61F 13/00* (2006.01)
(52) U.S. Cl. ........................ 424/449; 424/448
(58) Field of Classification Search .................. 424/449, 424/448
See application file for complete search history.

(56) References Cited

U.S. PATENT DOCUMENTS

| | | | |
|---|---|---|---|
| 4,322,400 A | 3/1982 | Yuhas | |
| 4,407,897 A * | 10/1983 | Farrell et al. .................. | 428/516 |
| 4,987,186 A | 1/1991 | Akiyama et al. | |
| 5,254,338 A | 10/1993 | Sakai et al. | |
| 5,399,362 A * | 3/1995 | Baichwal et al. .............. | 424/488 |
| 5,462,746 A | 10/1995 | Wolter et al. | |
| 5,480,649 A | 1/1996 | Akazawa et al. | |
| 5,645,855 A | 7/1997 | Lorenz | |
| 5,922,308 A | 7/1999 | Brewster et al. | |
| 6,121,508 A * | 9/2000 | Bischof et al. .................. | 602/52 |
| 6,139,867 A | 10/2000 | Muraoka et al. | |
| 6,146,656 A | 11/2000 | Hori et al. | |
| 6,884,434 B1 | 4/2005 | Muller et al. | |
| 7,557,230 B2 * | 7/2009 | Komuro et al. ............... | 556/173 |
| 2001/0006628 A1 | 7/2001 | Govil et al. | |
| 2004/0062759 A1 | 4/2004 | Abraham et al. | |

FOREIGN PATENT DOCUMENTS

| | | |
|---|---|---|
| CN | 1219874 A | 6/1999 |
| EP | 0 435 199 A2 | 7/1991 |
| EP | 0651984 B1 * | 4/1999 |
| EP | 0 931 546 A1 | 7/1999 |
| EP | 1 044 684 B1 | 10/2000 |
| JP | 01-178566 A | 7/1989 |
| JP | 08-291056 A | 11/1996 |
| JP | 09-132525 A | 5/1997 |
| JP | 11-209270 A | 8/1999 |
| JP | 11-209271 A | 8/1999 |
| JP | 2000-355535 A | 12/2000 |
| JP | 2001-181591 A | 7/2001 |
| JP | 2002-509878 A | 4/2002 |
| JP | 2002-258044 A | 9/2002 |
| JP | 2003-62058 A | 3/2003 |
| JP | 2004-10252 A | 1/2004 |
| RU | 99100389 A | 11/2000 |
| RU | 2 185 144 C2 | 7/2002 |
| WO | WO 96/40085 A2 | 12/1996 |
| WO | WO 01/43775 A2 | 6/2001 |

OTHER PUBLICATIONS

European Search Report dated Oct. 31, 2006.
Chinese Office Action dated Jun. 5, 2009, English language translation.
European Notice of Opposition dated Jul. 6, 2009.
Office Action issued Jun. 11, 2010 in counterpart Russian Application No. 2006119610/15(021311).
Canadian Office Action, dated Feb. 7, 2011, issued in Application No. 2,548,864.
Communication issued in counterpart European Application No. 06011300.8-2101 dated Oct. 12, 2010.
Office Action dated Oct. 7, 2010, issued in corresponding Russian Patent Application No. 2006119610/15.
Canadian Office Action dated Nov. 22, 2011 issued by the Canadian Intellectual Property Office in corresponding Canadian Application No. 2548864.
Communication drafted on Oct. 14, 2011 issued by the Japanese Patent Office in corresponding Japanese Application No. 2006-156586.
Notification of Reasons for Refusal Issued on Apr. 3, 2012 in Corresponding of 2006-156586.
Israeli Office Action issued in corresponding Israeli Patent Application No. 176032 on Apr. 13, 2011, Translation.
Third Party Observation, dated Apr. 28, 2009, issued in Japanese Application No. 2006-156586.
Third Party Observation, dated Apr. 19, 2011, issued in Japanese Application No. 2006-156586.
Korean Office Action dated Jun. 21, 2012 issued by the Korean Intellectual Property Office in corresponding Korean Patent Application No. 10-2006-0050286.
Office Action dated Dec. 26, 2012 issued by the Korean Intellectual Property Office in counterpart Korean Patent Application No. 10-2006-0050286.

* cited by examiner

*Primary Examiner* — Ali Soroush
(74) *Attorney, Agent, or Firm* — Sughrue Mion, PLLC

(57) ABSTRACT

A stable percutaneous absorption-type pharmaceutical preparation for percutaneous administration of drugs except for selegiline and selegiline hydrochloride, which does not suffer a decrease in the cohesive force of the adhesive layer therein even in the presence of sweat components due to perspiration during wear and which is free from cohesive failure and resultant adhesive remaining when stripped off. A percutaneous absorption-type pharmaceutical preparation which comprises: a support; and an adhesive layer containing an adhesive, a metal chloride and a percutaneously-absorptive drug except for selegiline and selegiline hydrochloride, wherein the adhesive layer is subjected to a crosslinking treatment.

7 Claims, No Drawings

PERCUTANEOUS ABSORPTION-TYPE PHARMACEUTICAL PREPARATION

FIELD OF THE INVENTION

The present invention relates to a percutaneous absorption-type pharmaceutical preparation not containing selegiline and selegiline hydrochloride. Concretely, it is a percutaneous absorption-type pharmaceutical preparation that is applied to the skin of a living body so as to continuously administer the percutaneously-absorptive drug into the body through the skin.

BACKGROUND OF THE INVENTION

Percutaneous absorption-type pharmaceutical preparations have many advantages in that they may evade drug absorption by digestive tubes and may evade initial drug passing through liver, that they are applicable even to persons for whom oral drug administration is difficult and that they may be effective for preventing forgetful drug administration, and recently, they have become much highlighted as excellent drug administration modes because of such their various advantages, and various types of percutaneous absorption-type pharmaceutical preparations have been developed.

Recently, some new functions have become imparted to some percutaneous absorption-type pharmaceutical preparations, for example, types of diseases (e.g., cardiopathy, etc.) applicable to percutaneous absorption-type pharmaceutical preparations are printed on the covers of the preparations, and even when patients have become under unconsciousness, erroneous drug administration (contraindicant drug administration) to them could be evaded, and further development of those percutaneous absorption-type pharmaceutical preparations in future is expected.

However, when asked as to whether any and every drug could be usable for percutaneous administration, in fact, it must be said that most drugs are unsuitable to percutaneous administration. There are many drugs in the form of their acidic salts such as hydrochlorides, but when such acidic salts are, as they are, directly formulated into percutaneous absorption-type pharmaceutical preparations, then their hydrophilic properties derived from salts may have a significant influence on the preparations. As a result, there are many cases where the drugs in the resultant preparations could hardly penetrate through a keratin layer that is in a hydrophilic environment, and therefore the preparations could not bring about a necessary drug concentration in blood. Regarding this, many techniques of converting acidic salt drugs in preparations into free-form drugs by the use of basic compounds (neutralization) have been investigated. In general, organic amines are utilized for the basic compounds in such techniques, but amino group-having polymer compounds are also utilized for them. Organic amines may be effective for neutralization, but they are relatively unstable by themselves and their purification is difficult. Therefore, they are problematic in that their purity is low and they may color drugs or may often decompose drugs. On the other hand, regarding amino group-having polymer compounds, their amount necessary for neutralization of drugs is larger than that of low-molecular compounds of organic amines, or that is, a larger amount of such a polymer compound must be added for the necessary neutralization. Another problem with them is that such polymer compounds could not have good adhesiveness, and therefore when they are added to percutaneous absorption-type pharmaceutical preparations, then they may lower the adhesiveness of the preparations. The adhesiveness thereof is the second important factor of percutaneous absorption-type pharmaceutical preparations, next to the most important factor thereof of drug permeability. In case where the adhesiveness of a percutaneous absorption-type pharmaceutical preparation applied to a minor disease is poor and where the preparation is readily stripped away because of the poor adhesiveness, then it would be unexpected that the patient's disease might be soon worse. However, when the same has occurred in a patient suffering from a serious disease, then it would soon result in a serious problem.

Regarding drug administration for diseases, the administration period is preferably shorter, but in real life, drugs are often administered for a long period of time. In case where a percutaneous absorption-type pharmaceutical preparation is applied during such a long-term administration period, then the administration shall be repeated almost everyday. Recently, 3-days lasting preparations and 1-week lasting preparations are being developed for practical use. The site to which a percutaneous absorption-type pharmaceutical preparation is applied is preferably one except the moving sites of a body especially for preventing the problem of stripping, and it is understood that percutaneous absorption-type pharmaceutical preparations are limited in point of the applicable site thereof. Regarding their types, various types such as reservoir-type or matrix-type of percutaneous absorption-type pharmaceutical preparations are known. However, they could not still solve the problem of their applicability to limited sites. In addition, the influence of users' feeling in application and especially stripping of those percutaneous absorption-type pharmaceutical preparations on the users' bodies is significantly great.

On the assumption of repeated application thereof from the above, percutaneous absorption-type pharmaceutical preparations are required to be as soft as possible to the skin so as not to irritate the skin surface to cause keratin damage, or that is, the preparations are desired to be less irritative. Regarding it, there may be mentioned a method of changing the composition of the adhesive itself to be employed so as to suitably lower the adhesive power thereof to the skin, or a method of making the adhesive layer gel by adding a liquid ingredient thereto so that the adhesive layer may have a soft touch. For the gel formation, a method has heretofore been employed, which comprises adding a crosslinking agent to an adhesive to increase the cohesive force thereof so that the adhesive layer may hold a liquid ingredient miscible therein.

Regarding the gel formation, however, when a basic drug is used in a percutaneous absorption-type pharmaceutical preparation, then it may react with a polyfunctional isocyanate or the like compound used as a crosslinking agent therein, and the crosslinking agent could not sufficiently exhibit its function. In such a case, it is known that a metal chelate or the like crosslinking agent may act predominantly, therefore exhibiting its effect.

Recently, however, it has been known that when a percutaneous absorption-type pharmaceutical preparation that comprises a gel of a combination of a basic drug and a metal chelate is applied to humans, then the crosslinked sites in the adhesive layer may be broken by lactic acid, a minor component of sweat perspiring through sweat glands, therefore causing cohesive failure in stripping the pharmaceutical preparation.

Regarding it, methods have been proposed for evading the problem; one comprising adding another component of polyalcohol so as to more conveniently exhibit the intrinsic effect of the metal chelate (Patent Reference 1: JP-A 2003-62058), and the other comprising planning a placebo layer that comprises a crosslinking agent not influenced by lactic acid for the adhesive layer to be in direct contact to the skin followed by superposing, as an upper layer thereon, an adhesive layer that contains a basic drug and is crosslinked with a metal chelate (Patent Reference 2: JP-A 2004-10525).

However, in the former method (Patent Reference 1), since the polyalcohol is a hydrophilic compound, it may uniformly dissolve in the adhesive layer that is in a hydrophobic environment, only in some degree (up to about 5%), and when its amount exceeds the limit, then there may occur a problem of its blooming from the adhesive layer. Accordingly, it has been found that, when a relatively large amount of a basic drug is incorporated in the adhesive layer, then a necessary amount of a polyalcohol could not be incorporated therein.

Regarding the latter method (Patent Reference 2), the cohesion failure on stripping, which is caused by the penetration and diffusion of lactic acid into the skin through the attached surface of the preparation, could be prevented, but in fact, since the sides of the percutaneous absorption-type pharmaceutical preparation are in contact with the skin in its application to the skin, it has been found that the occurrence of remarkable cohesion failure at the edges of the preparation owing to the penetration of lactic acid trough the sides thereof could not be evaded.

SUMMARY OF THE INVENTION

In consideration of the above-mentioned situation, an object of the invention is to provide a stable percutaneous absorption-type pharmaceutical preparation for percutaneous administration of basic drugs except for selegiline and selegiline hydrochloride, which does not suffer a decrease in the cohesive force of the adhesive layer therein even in the presence of sweat components due to perspiration during wear and which is free from cohesive failure and resultant adhesive remaining when stripped off.

The present inventors made intensive investigations in order to accomplish the object. As a result, they have found that, when a metal chloride is added to an adhesive layer containing a basic drug except for selegiline and selegiline hydrochloride, then the reduction in the cohesive force of the adhesive layer having taken lactic acid in sweat therein may be prevented. Thus, the present invention has been completed.

The invention provides the following.
(1) A percutaneous absorption-type pharmaceutical preparation which comprises: a support; and an adhesive layer containing an adhesive, a metal chloride and a percutaneously-absorptive drug except for selegiline and selegiline hydrochloride, wherein the adhesive layer is subjected to a crosslinking treatment.
(2) The percutaneous absorption-type pharmaceutical preparation of (1), wherein the crosslinking treatment is performed by a metal chelate compound.
(3) The percutaneous absorption-type pharmaceutical preparation of (1) or (2), wherein the percutaneously-absorptive drug is a basic drug.
(4) The percutaneous absorption-type pharmaceutical preparation of any one of (1) to (3), wherein the adhesive includes an acrylic polymer adhesive.
(5) The percutaneous absorption-type pharmaceutical preparation of any one of (1) to (4), wherein the metal chloride includes at least one inorganic metal chloride selected from the group consisting of sodium chloride, aluminium chloride, stannous chloride and ferric chloride.
(6) The percutaneous absorption-type pharmaceutical preparation of any one of above (1) to (4), wherein the metal chloride is sodium chloride.
(7) The percutaneous absorption-type pharmaceutical preparation of any one of above (1) to (6), wherein the metal chloride is a salt formed by neutralizing a hydrochloride of a basic drug, which is the percutaneously-absorptive drug, with a basic compound.
(8) The percutaneous absorption-type pharmaceutical preparation of any one of (1) to (7), wherein the adhesive layer further contains a liquid plasticizer.
(9) The percutaneous absorption-type pharmaceutical preparation of (8), wherein the liquid plasticizer is a fatty acid ester of a higher fatty acid having from 12 to 16 carbon atoms and a lower monoalcohol having from 1 to 4 carbon atoms.

The percutaneous absorption-type pharmaceutical preparation of the invention can prevent the reduction in the cohesive force of the adhesive layer therein to be caused by infiltration of lactic acid, a sweat component, into it. Accordingly, the invention provides a stable absorption-type pharmaceutical preparation, in which the content of the drug (that is, basic drug except for selegiline and selegiline hydrochloride) in the adhesive layer can be set freely, and which does not suffer a decrease in the cohesive force of the adhesive layer therein even in the presence of sweat components due to perspiration during wear and is free from cohesive failure and resultant adhesive remaining when stripped off.

DETAILED DESCRIPTION OF THE INVENTION

The invention is described in detail hereinunder.

The support to be used in the invention is not particularly limited. However, it is preferably made of a material which prevents the drug and the liquid plasticizer in the preparation from passing through the support and going out from its back side to result in a decrease in their content. Namely, the support is preferably made of a material impermeable to these ingredients. Concretely, it includes films of polyesters, nylons, polyvinyl chlorides, polyethylenes, polypropylenes, ethylene-vinyl acetate copolymers, polytetrafluoroethylenes, ionomer resins; and metal foils, and their laminate films. Of those, laminate films of a poreless film and a porous film of the above-mentioned material are preferred for the support and the adhesive layer is formed on the porous film in order to improve the adhering capability (anchoring capability) of the support to the adhesive layer.

The porous film is not particularly limited so far as its anchoring capability for the adhesive layer to be thereon is good. For example, it includes paper, woven fabrics, nonwoven fabrics, mechanically-perforated sheets. In particular, paper, woven fabrics and nonwoven fabrics are preferred. The thickness of the porous film may be generally from 10 to 500 µm in consideration of improving the anchoring capability of the film and of the flexibility of the percutaneous absorption-type pharmaceutical preparation. For thin percutaneous absorption-type pharmaceutical preparations such as plaster-type or adhesive tape-type ones, the thickness of the porous film may be generally from 10 to 200 µm or so. When the porous film is formed of a woven fabric or nonwoven fabric, then its basis weight may be preferably from 5 to 30 g/m² for improving the anchoring capability of the film.

The adhesive in the adhesive layer to be formed on at least one side of the support is not also particularly limited. Preferably, it is formed of a copolymer prepared through copolymerization of an alkyl (meth)acrylate as the essential ingredient thereof. Preferably, the alkyl group of the alkyl (meth) acrylate has at least 4 carbon atoms, and may be linear or branched. Concretely, it includes butyl, pentyl, hexyl, heptyl, octyl, 2-ethylhexyl, nonyl, decyl, undecyl, dodecyl, tridecyl. One or more such alkyl (meth)acrylates may be used herein either singly or as combined.

The monomer capable of copolymerizing with the alkyl (meth)acrylate includes, for example, carboxyl group-having monomers and anhydride thereof such as (meth)acrylic acid, itaconic acid, maleic acid, maleic anhydride; sulfonic acid monomers such as styrenesulfonic acid, allylsulfonic acid, sulfopropyl (meth)acrylate, (meth)acryloyloxynaphthalenesulfonic acid, acrylamidomethylsulfonic acid; hydroxyl group-having monomers such as hydroxypropyl (meth)acrylate; amido group-having (meth)acrylic acid derivatives such as (meth)acrylamide, dimethyl(meth)acrylamide, N-butyl (meth)acrylamide, N-methylol(meth)acrylamide; aminoalkyl(meth)acrylates such as aminoethyl(meth)acrylate, dimethylaminoethyl(meth)acrylate, t-butylaminoethyl (meth)acrylate; alkoxy (meth)acrylates such as methoxyethyl (meth)acrylate, ethoxyethyl (meth)acrylate, tetrahydrofurfuryl (meth)acrylate; alkoxyalkylene glycol (meth)acrylates such as methoxyethylene glycol (meth)acrylate, methoxydiethylene glycol (meth)acrylate, methoxypolyethylene glycol (meth)acrylate, methoxypolypropylene glycol (meth)acrylate; (meth)acrylonitrile; vinyl-having compounds such as vinyl acetate, vinyl propionate, methylvinylpyrrolidone, vinylpyridine, vinylpiperidone, vinylpyrimidine, vinylpiperazine, vinylpyrrole, vinylimidazole, vinylcaprolactam, vinyloxazole, vinylmorpholine. One or more of these may be used herein either singly or as combined. The copolymerization of those monomers may be suitably determined depending on the weight-average molecular weight of the resulting copolymers. Acrylic copolymer adhesives concretely include, for example, copolymers of 2-ethylhexyl acrylate, N-vinyl-2-pyrrolidone and acrylic acid; and copolymers of 2-ethylhexyl acrylate, 2-hydroxyethyl acrylate and vinyl acetate.

Though varying depending on the copolymerization composition thereof, the glass transition temperature of the acrylic adhesive may be, in general, preferably from −60 to −10° C., more preferably from −43 to −27° C.

The adhesive layer in the invention may contain a rubber-based adhesive, a silicone-based adhesive, a vinyl ester-based adhesive and the like, in addition to the acrylic adhesive.

The adhesive layer of the percutaneous absorption-type pharmaceutical preparation of the invention contains a metal chloride. Concretely, the metal chloride is preferably an inorganic metal chloride including, for example, sodium chloride, aluminium chloride, stannous chloride, ferric chloride. Any one of these or two or more of these may be used herein either singly or as combined. Preferably, sodium chloride is used.

The metal chloride content of the layer may be preferably from 0.1 to 20 parts by weight, more preferably from 1 to 10 parts by weight, per 100 parts by weight of the adhesive polymer in the layer. When the content is smaller than 0.1 parts by weight, then the effect of inhibiting the influence of lactic acid in sweat on the pharmaceutical preparation may be insufficient; but on the contrary, when the content is larger than 20 parts by weight, then the inhibiting effect may be enough but the metal chloride could not uniformly disperse in the adhesive, therefore often causing a problem of bad appearance of the pharmaceutical preparation.

A liquid plasticizer may be added to the adhesive layer.

The liquid plasticizer is not particularly limited as long as it is liquid by itself at room temperature and has a plasticizing effect and is compatible with the adhesive polymer mentioned above. Preferably, it may improve the percutaneous absorbability and the storage stability of drugs. Concretely, the liquid plasticizer includes fatty acid esters of a higher fatty acid having from 12 to 16 carbon atoms and a lower monoalcohol having from 1 to 4 carbon atoms; fatty acids having from 8 to 10 carbon atoms; glycols such as ethylene glycol, diethylene glycol, triethylene glycol, polyethylene glycol, propylene glycol, polypropylene glycol; oils and fats such as olive oil, castor oil, squalane, lanolin; organic solvents such as ethyl acetate, ethyl alcohol, dimethyldecyl sulfoxide, methyloctyl sulfoxide, dimethyl sulfoxide, dimethylformamide, dimethylacetamide, dimethyllaurylamide, dodecylpyrrolidone, isosorbitol; liquid surfactants; known plasticizers such as diisopropyl adipate, phthalates, diethyl sebacate; hydrocarbons such as liquid paraffin; and others such as ethoxylated stearyl alcohol, glycerin esters (that are liquid at room temperature), isopropyl myristate, isotridecyl myristate, ethyl laurate, N-methylpyrrolidone, ethyl oleate, oleic acid, diisopropyl adipate, diisopropyl palmitate, octyl palmitate, 1,3-propanediol, glycerin. Needless-to-say, those that are liquid at room temperatures are used herein. One or more of those are used herein either singly or as combined.

Further, in consideration of improving the percutaneous absorbability of drugs, the above-mentioned fatty acid may be combined with a fatty acid having from 8 to 10 carbon atoms and/or glycerin for use herein. The fatty acid having from 8 to 10 carbon atoms includes, for example, caprylic acid (octanoic acid, C8), pelargonic acid (nonanoic acid, C9), capric acid (decanoic acid, C10).

The amount of the liquid plasticizer to be incorporated is preferably from 10 to 140 parts by weight, more preferably from 40 to 100 parts by weight, per 100 parts by weight of the adhesive polymer. When the amount of the liquid plasticizer incorporated is smaller than 10 parts by weight, then the plasticization of the adhesive layer may be insufficient and the skin irritation of the pharmaceutical preparation could not be reduced. On the contrary, when the amount thereof is larger than 140 parts by weight, then the liquid plasticizer could not be held in the adhesive layer even by the cohesive force of the adhesive polymer therein and it may bloom out on the surface of the adhesive layer to lower the adhesiveness of the layer.

The crosslinking agent for crosslinking the adhesive layer may be a crosslinking agent of which the ability to form crosslinks is not retarded by percutaneously-absorptive drugs except for selegiline and selegiline hydrochloride. For example, it includes organometallic compounds (e.g., zirconium and zinc, zinc acetate, zinc ammonium glycinate); metal alcoholates (e.g., tetraethyl titanate, tetraisopropyl titanate, aluminium isopropylate, aluminium butyrate), and metal chelate compounds (e.g., di-i-propoxybis(acetylacetone) titanate, tetraoctylene glycol titanate, aluminium isopropylate, (ethyl acetoacetate) aluminium diisopropylate, aluminium tris(ethyl acetoacetate), aluminium tris(acetylacetate)). One or more such crosslinking agents may be used either singly or as combined.

Though varying depending on the type of the crosslinking agent and the adhesive used, the amount of the crosslinking agent to be incorporated may be generally from 0.1 to 0.6 parts by weight, preferably from 0.15 to 0.4 parts by weight, per 100 parts by weight of the adhesive.

The gel fraction of the percutaneous absorption-type pharmaceutical preparation of the invention is preferably at least 45%, more preferably at least 55%, from the viewpoint of the sustainability of the cohesive force of the adhesive therein.

Not particularly limited, the drug to be in the adhesive layer in the invention may be any one capable of being percutaneously absorbed but excepting selegiline and selegiline hydrochloride. Preferably, it is a basic drug. The drug may also be in the form of its pharmaceutically-acceptable salt, including, for example, acidic salts of basic drugs, such as hydrochlorides, nitrates, succinates, fumarates, tartrates, salicylates, sulfates and phosphates thereof.

Concretely, for example, the drug includes hypnotic sedatives (e.g., flurazepam, rilmazafone and their hydrochlorides), antipyretic anti-inflammatory analgesics (e.g., butorphanol tartrate, perisoxal citrate), stimulants (e.g., methamphetamine, methylphenidate and their hydrochlorides), drugs for psychoneurosis (e.g., chlorpromadine, imiplamine and their hydrochlorides), topical anesthetics (lidocaine, procaine and their hydrochlorides), drugs for urinary systems (e.g., oxybutynin and its hydrochloride), skeletal muscular relaxants (e.g., tizanidine, eperisone and their hydrochlorides, pridinol mesylate), drugs for autonomic nervous systems (e.g., carpronium and its hydrochloride, neostigmine bromide), antiparkinsonian drugs (e.g., trihexyphenidyl, amantadine and their hydrochlorides), antihistaminics (e.g., clemastine fumarate, diphenhydramine tannate), bronchodilators (e.g., tulobuterol, procaterol and their hydrochlorides), cardiacs (e.g., isoprenaline, dopamine and their hydrochlorides), coronary vasodilators (e.g., diltiazem, verapamil, gallopamil and their hydrochlorides), peripheral vasodilators (e.g., nicametate citrate, tolazoline, tolazoline hydrochloride), drugs for circulatory systems (e.g., flunarizine, nicardipine and their hydrochlorides), drugs for arrhythmia (e.g., propranolol, alprenolol and their hydrochlorides), antiallergics (e.g., ketofetin fumarate, azelastine), antivertiginous drugs (e.g., betahistine mesylate, diphenidol, diphenidol hydrochloride), serotonin receptor-antagonistic antiemetics, anesthetic sedatives (e.g., morphine sulfate, fentanyl citrate). One or more such drugs may be used herein either singly or as combined.

The content of the drug in the percutaneous absorption-type pharmaceutical preparation of the invention may be suitably set depending on the type of the drug and the object for administration. In general, it may be preferably from 0.1% by weight to 60% by weight in the adhesive layer, more preferably from 2% by weight to 30% by weight. When the amount of the drug in the adhesive layer is smaller than 0.1% by weight, then it is unfavorable since the preparation could not release the drug in an amount effective for remedy. Even when the amount of the drug in the adhesive layer is larger than 60% by weight, the drug increase could not result in further increase in therapeutical effect and would be uneconomical, and it is therefore also unfavorable.

The thicknesses of the adhesive layer may be generally from 10 to 300 µm, preferably from 60 to 150 µm, from the stand point of the applicability to the skin and the strippability of the pharmaceutical preparation.

If desired, additives may be incorporated into the adhesive layer. Examples thereof include antioxidants, various pigments, various fillers, stabilizers, drug dissolution aids, and drug dissolution inhibitors.

Not particularly limited in point of its production, the percutaneous absorption-type pharmaceutical preparation of the invention may be produced, for example, according to the following production method.

A percutaneously-absorptive drug except for selegiline and selegiline hydrochloride is mixed with stirring with a metal chloride dispersed in a solvent such as ethanol to prepare a drug-containing liquid. In case where the drug is a hydrochloride, then the drug (hydrochloride) may be mixed with stirring with a basic compound such as a metal hydroxide in a solvent for neutralization to form a metal chloride. (In other words, a drug-containing liquid that contains a metal chloride may be prepared in this case.) Further, after a drug (hydrochloride) is mixed with stirring with a basic compound such as a metal hydroxide in a solvent to form an inorganic metal chloride therein, another metal chloride may be added to the resultant drug-containing liquid. The metal hydroxide includes, for example, sodium hydroxide, calcium hydroxide, magnesium hydroxide. Sodium hydroxide is preferably used.

The drug-containing liquid is dissolved or dispersed in a solvent or dispersant, for example, along with an adhesive (e.g., acrylic copolymer adhesive), a crosslinking agent and optionally a liquid plasticizer and other additives therein. Not particularly limited, the solvent or the dispersant to be used in forming the adhesive layer may be any ordinary one generally used as a solvent or the like for adhesives, and may be selected in consideration of the type of the adhesive used and the reactivity thereof with drugs. For example, it includes ethyl acetate, toluene, hexane, 2-propanol, methanol, ethanol.

Next, the resultant solution or dispersion is applied onto one side of a support or onto the lubricant-processed side of a release sheet, and dried to form an adhesive layer thereon, and then, this is stuck to a release sheet or a support. Not particularly limited, the release sheet may be any one capable of being readily stripped from the adhesive layer in use. For example, for it, use may be made of a film of a polyester, polyvinyl chloride, polyvinylidene chloride, polyethylene terephthalate or the like in which the side to be in contact with the adhesive layer has been treated with a silicone, or of a laminated film obtained by laminating a polyolefin to wood-free paper or glassine paper. The thickness of the release sheet may be generally 200 µm or smaller, preferably from 25 to 100 µm. Such a release sheet is stuck to the adhesive layer and aged generally at 60 to 70° C. for 24 to 48 hours to promote the crosslinking in the layer, there by producing the percutaneous absorption-type pharmaceutical preparation of the invention.

Apart from the above, another production method may also be employed herein, which comprises dissolving or dispersing a percutaneously-absorptive drug in a solvent or dispersant along with an adhesive (e.g., acrylic copolymer adhesive), a crosslinking agent and optionally a liquid plasticizer and other additives therein to prepare a drug-containing liquid, then adding a metal chloride to the resultant liquid with stirring, applying it onto one side of a support or onto the lubricant-processed side of a release sheet, drying it to form an adhesive layer thereon, and thereafter sticking it to a release sheet or a support.

The shape of the percutaneous absorption-type pharmaceutical preparation of the invention is not particularly limited. Examples thereof include tape forms and sheet forms.

The dose of the percutaneous absorption-type pharmaceutical preparation of the invention varies depending on the kind of the drug used, the age, body weight, and condition of the patient, etc. Usually, however, the dose for an adult is such that the pharmaceutical preparation containing from 5 to 100 mg of a percutaneously-absorptive drug is applied to a skin area of from 5 to 100 $cm^2$, about once per day or once per 2 days.

EXAMPLES

The invention will be described below in more detail with reference to the following Examples, but the invention should not be construed as being limited by these in any way. In the following description, all parts and percents are by weight.

Preparation of Acrylic Copolymer Adhesive A

In an inert gas atmosphere, 75 parts of 2-ethylhexyl acrylate, 22 parts of N-vinyl-2-pyrrolidone, 3 parts of acrylic acid and 0.2 parts of azobisisobutyronitrile were subjected to solution polymerization in ethyl acetate at 60° C. to prepare a solution of an acrylic copolymer A.

Preparation of Acrylic Copolymer Adhesive B

In an inert gas atmosphere, 95 parts of 2-ethylhexyl acrylate, 5 parts of acrylic acid and 0.2 parts of benzoyl peroxide were subjected to solution polymerization in ethyl acetate at 60° C. to prepare a solution of an acrylic copolymer B.

Example 1

49 parts of the acrylic adhesive A, 40 parts of isopropyl myristate and 10 parts of gallopamil were mixed and stirred in a container to give a uniform mixture. Next, 1 part of sodium chloride dispersed in ethanol was added to the resultant acrylic adhesive A solution, and stirred. 0.3 parts (relative to the adhesive solid content) of (ethyl acetoacetate) aluminium diisopropylate was added to it, and the viscosity of the resultant mixture was controlled with ethyl acetate added thereto, and this was applied to a polyester film (75 μm thick) so that its dry thickness thereon could be 80 μm, and dried. This was stuck to a polyester film (12 μm thick), and aged at 70° C. for 48 hours to obtain a gallopamil-containing percutaneous absorption-type pharmaceutical preparation.

Example 2

47 parts of the acrylic adhesive A, 40 parts of isopropyl myristate and 10 parts of gallopamil were mixed and stirred in a container to give a uniform mixture. Next, 3 parts of sodium chloride dispersed in ethanol was added to the resultant acrylic adhesive A solution, and stirred. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Example 3

45 parts of the acrylic adhesive A, 40 parts of isopropyl myristate and 10 parts of gallopamil were mixed and stirred in a container to give a uniform mixture. Next, 5 parts of sodium chloride dispersed in ethanol was added to the resultant acrylic adhesive A solution, and stirred. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Example 4

48.42 parts of the acrylic adhesive A and 40 parts of isopropyl myristate were mixed and stirred in a container to give a uniform mixture. In a different container, 10.75 parts of gallopamil hydrochloride was mixed with 0.83 parts of sodium hydroxide (10% by weight) dissolved in ethanol, with stirring. The resultant sodium chloride and free gallopamil were added to the previous acrylic adhesive A solution, and stirred. 0.3 parts (relative to the adhesive solid content) of (ethyl acetoacetate) aluminium diisopropylate was added to it, and the viscosity of the resultant mixture was controlled with ethyl acetate added thereto, and this was applied to a polyester film (75 μm thick) so that its dry thickness thereon could be 80 μm, and dried. This was stuck to a polyester film (12 μm thick), and aged at 70° C. for 48 hours to obtain a gallopamil-containing percutaneous absorption-type pharmaceutical preparation.

Example 5

36.84 parts of the acrylic adhesive A and 40 parts of isopropyl myristate were mixed and stirred in a container to give a uniform mixture. In a different container, 21.5 parts of gallopamil hydrochloride was mixed with 1.66 parts of sodium hydroxide (10% by weight) dissolved in ethanol, with stirring. The resultant sodium chloride and free gallopamil were added to the previous acrylic adhesive A solution, and stirred. 0.3 parts (relative to the adhesive solid content) of (ethyl acetoacetate) aluminium diisopropylate was added to it, and the viscosity of the resultant mixture was controlled with ethyl acetate added thereto, and this was applied to a polyester film (75 μm thick) so that its dry thickness thereon could be 80 μm, and dried. This was stuck to a polyester film (12 μm thick), and aged at 70° C. for 48 hours to obtain a gallopamil-containing percutaneous absorption-type pharmaceutical preparation.

Example 6

47 parts of the acrylic adhesive B, 40 parts of isopropyl myristate and 10 parts of gallopamil were mixed and stirred in a container to give a uniform mixture. Next, 3 parts of sodium chloride dispersed in ethanol was added to the resultant acrylic adhesive B solution, and stirred. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Example 7

48.16 parts of the acrylic adhesive A and 40 parts of isopropyl myristate were mixed and stirred in a container to give a uniform mixture. In a different container, 10.88 parts of diltiazem hydrochloride was mixed with 0.96 parts of sodium hydroxide (10% by weight) dissolved in ethanol, with stirring. The resultant sodium chloride and free diltiazem were added to the previous acrylic adhesive A solution, and stirred. 0.3 parts (relative to the adhesive solid content) of (ethyl acetoacetate) aluminium diisopropylate was added to it, and the viscosity of the resultant mixture was controlled with ethyl acetate added thereto, and this was applied to a polyester film (75 μm thick) so that its dry thickness thereon could be 80 μm, and dried. This was stuck to a polyester film (12 μm thick), and aged at 70° C. for 48 hours to obtain a diltiazem-containing percutaneous absorption-type pharmaceutical preparation.

Reference Example 1

51 parts of the acrylic adhesive A, 40 parts of isopropyl myristate, 4 parts of gallopamil and 5 parts of glycerin were mixed and stirred in a container to give a uniform mixture. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 1

50 parts of the acrylic adhesive A, 40 parts of isopropyl myristate and 10 parts of gallopamil were mixed and stirred in a container to give a uniform mixture. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 2

45 parts of the acrylic adhesive A, 40 parts of isopropyl myristate, 10 parts of gallopamil and 5 parts of glycerin were mixed and stirred in a container to give a uniform mixture. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 3

50 parts of the acrylic adhesive B, 40 parts of isopropyl myristate and 10 parts of gallopamil were mixed and stirred in a container to give a uniform mixture. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 4

45 parts of the acrylic adhesive B, 40 parts of isopropyl myristate, 10 parts of gallopamil and 5 parts of glycerin were mixed and stirred in a container to give a uniform mixture. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 5

43.5 parts of the acrylic adhesive A, 40 parts of isopropyl myristate and 3 parts of glycerin were mixed and stirred in a container to give a uniform mixture. In a different container, 10.75 parts of gallopamil hydrochloride and 2.75 parts of diisopropanolamine (both in 2-propanol solution controlled to 10% by weight) were mixed with stirring, and added to the previous acrylic adhesive A solution and stirred. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 6

30 parts of the acrylic adhesive A, 40 parts of isopropyl myristate and 3 parts of glycerin were mixed and stirred in a container to give a uniform mixture. In a different container, 21.5 parts of gallopamil hydrochloride and 5.5 parts of diisopropanolamine (both in 2-propanol solution controlled at 10% by weight) were mixed with stirring, and added to the previous acrylic adhesive A solution and stirred. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 7

42.99 parts of the acrylic adhesive A, 40 parts of isopropyl myristate and 5 parts of glycerin were mixed and stirred in a container to give a uniform mixture. In a different container, 10.75 parts of gallopamil hydrochloride and 1.26 parts of monoethanolamine (both in 2-propanol solution controlled at 10% by weight) were mixed with stirring, and added to the previous acrylic adhesive A solution and stirred. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 8

42.99 parts of the acrylic adhesive B, 40 parts of isopropyl myristate and 5 parts of glycerin were mixed and stirred in a container to give a uniform mixture. In a different container, 10.75 parts of gallopamil hydrochloride and 1.26 parts of monoethanolamine (both in 2-propanol solution controlled at 10% by weight) were mixed with stirring, and added to the previous acrylic adhesive B solution and stirred. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a gallopamil-containing percutaneous absorption-type pharmaceutical preparation.

Comparative Example 9

45 parts of the acrylic adhesive A, 40 parts of isopropyl myristate, 10 parts of diltiazem and 5 parts of glycerin were mixed and stirred in a container to give a uniform mixture. 0.3 parts (relative to the adhesive solid content) of (ethyl acetoacetate) aluminium diisopropylate was added to it, and the viscosity of the resultant mixture was controlled with ethyl acetate added thereto. This was processed in the same manner as in Example 1 to obtain a diltiazem-containing percutaneous absorption-type pharmaceutical preparation.

Experimental Examples

The gallopamil or diltiazem-containing percutaneous absorption-type pharmaceutical preparations produced in the above Examples and Comparative Examples were tested as in the gel fraction measurement test and the dipping test mentioned below.

Experimental Example 1

Gel Fraction Measurement Test

The proportion of the gel component insoluble in ethyl acetate, remaining in the preparations, was determined according to the method mentioned below.

The preparation was punched out to give 25-cm² pieces (5 cm×5 cm). Two pieces were stuck to a porous tetrafluoroethylene film (20 cm×10 cm) (substrate) of which the weight had been previously measured. This was folded so that the contents could not drop from it, and its weight was measured. This was put into a beaker. Two different types of solvents (type 1: ethyl acetate, type 2: ethyl acetate with 0.4 wt. % lactic acid) were separately added to the beakers so that the substrate could be completely immersed therein. On the next day, the solution in each beaker was removed, the same solvent as that used in the previous day was added to it. The solvent was exchanged everyday. After three exchanges, the solution in each beaker was removed, and the sample was dried, and its weight was measured. The gel fraction in the tested sample is calculated according to the following formula:

Gel Fraction (%)=100×((sample weight after drying–substrate weight–support weight)–(weight of sodium chloride in preparation))/((sample weight before drying–substrate weight–support weight)×(proportion of adhesive component in preparation))

Experimental Example 2

Dipping Test

On the assumption of actual application thereof to the skin, the cohesive force of the adhesive layer was determined according to the method mentioned below.

The preparation was punched out to give 10-cm² pieces (3.16 cm×3.16 cm). 5 ml of 0.4 wt. % lactic acid-containing physiological saline was put into a laboratory dish of glass, and the punched piece was, after its separator had been stripped off, dipped in the saline so that its adhesive side could face downward (the sample piece floated in the saline). After dipped for 24 hours, the sample piece was taken out, and its surface was dried. Panelists touched the dry surface with their fingers, and evaluated the tested samples.

The results in Experimental Examples 1 and 2 are given in Table 1.

TABLE 1

| | Gel Fraction (%) Type 1 | Gel Fraction (%) Type 2 | Evaluation before and after dipping |
|---|---|---|---|
| Example 1 | 85.8 | 55.1 | no cohesive failure |
| Example 2 | 90.0 | 61.4 | no cohesive failure |
| Example 3 | 92.9 | 71.6 | no cohesive failure |
| Example 4 | 86.9 | 57.7 | no cohesive failure |
| Example 5 | 88.3 | 63.5 | no cohesive failure |
| Example 6 | 86.0 | 52.7 | no cohesive failure |
| Example 7 | 76.5 | 55.8 | no cohesive failure |
| Reference Example | 84.1 | 53.7 | no cohesive failure |
| Comparative Example 1 | 83.8 | 21.6 | no cohesive failure |
| Comparative Example 2 | 79.6 | 18.7 | cohesive failure |
| Comparative Example 3 | 87.6 | 25.4 | cohesive failure |
| Comparative Example 4 | 86.1 | 21.0 | cohesive failure |
| Comparative Example 5 | 84.6 | 12.7 | cohesive failure |
| Comparative Example 6 | 85.2 | 6.5 | cohesive failure |
| Comparative Example 7 | 89.4 | 8.7 | cohesive failure |
| Comparative Example 8 | 94.9 | 14.5 | cohesive failure |
| Comparative Example 9 | 75.2 | 5.3 | cohesive failure |

The results in Table 1 confirm the following: The data of gel fraction in type 1 may indicate that the tested samples could seemingly keep their crosslinked structures. However, as in the test with type 2 in which lactic acid, a component of sweat, was added to ethyl acetate, on the assumption of actual application of the preparations to the skin, the samples of Examples 1 to 7 kept a value of more than 50%, though lower than the value in the test with type 1. As understood from the test data before and after dipping, it has been confirmed that the adhesive layer does not suffer cohesive failure so far as it keeps the gel fraction level as in these Examples. In addition, it is also understood that, when the sodium chloride concentration in the preparations is increased, then the gel fraction level further increases.

When the concentration of the basic drug in the preparation is relatively low, then glycerin may be effective, as in Reference Example. However, it has been confirmed that, when the concentration of the basic drug is twice or more (Comparative Examples 1 to 4), then glycerin is no more effective and the adhesive layer suffers cohesive failure.

It is understood that, in Comparative Examples 2 and 4 in which glycerin was added but sodium chloride was not in the adhesive layer, the value significantly lowered and the adhesive layer suffered cohesive failure.

In Comparative Examples 5 to 8, in which an organic amine but not sodium hydroxide was added to the basic compound, the gel fraction value significantly lowered in the type-2 test and the adhesive layer suffered cohesive failure, like in the above-mentioned Comparative Examples.

In case where the concentration of the basic drug in the preparations is high, the amount of sodium chloride formed therein increased with the increase in the basic drug in Examples 4 and 5 and therefore the adhesive layer formed could have a higher cohesive force. However, as opposed to this, in Comparative Example 6, the gel fraction value in the type-2 test lowered with the increase in the drug concentration, and it has been confirmed that the cohesive failure could not be evaded in this case.

From the results in Example 7 and Comparative Example 9, it has been confirmed that the invention is effective for basic drugs that may be in the form of their hydrochlorides.

This application is based on Japanese patent application JP 2005-165213, filed on Jun. 6, 2005, the entire content of which is hereby incorporated by reference, the same as if set forth at length.

What is claimed is:

1. A percutaneous pharmaceutical preparation which comprises: a support; and an adhesive layer containing an adhesive, a metal chloride and a basic drug except for selegiline and selegiline hydrochloride, wherein the adhesive layer is subjected to a crosslinking treatment, wherein the crosslinking treatment is performed by a metal chelate compound.

2. The percutaneous pharmaceutical preparation of claim 1, wherein the adhesive includes an acrylic polymer adhesive.

3. The percutaneous pharmaceutical preparation of claim 1, wherein the metal chloride is at least one inorganic metal chloride selected from the group consisting of sodium chloride, aluminium chloride, stannous chloride and ferric chloride.

4. The percutaneous pharmaceutical preparation of claim 1, wherein the metal chloride is sodium chloride.

5. The percutaneous pharmaceutical preparation of claim 1, wherein the metal chloride is a salt formed by neutralizing a hydrochloride of a basic drug, which is the percutaneously-absorptive drug, with a basic compound.

6. The percutaneous pharmaceutical preparation of claim 1, wherein the adhesive layer further contains a liquid plasticizer.

7. The percutaneous pharmaceutical preparation of claim 6, wherein the liquid plasticizer is a fatty acid ester of a higher fatty acid having from 12 to 16 carbon atoms and a lower monoalcohol having from 1 to 4 carbon atoms.

* * * * *